(12) United States Patent
Green

(10) Patent No.: US 10,220,161 B2
(45) Date of Patent: Mar. 5, 2019

(54) GAS REMOVAL SYSTEMS AND METHODS

(71) Applicant: Richard Green, Santa Monica, CA (US)

(72) Inventor: Richard Green, Santa Monica, CA (US)

(73) Assignee: AILNH, LLC, Boca Raton, FL (US)

( * ) Notice: Subject to any disclaimer, the term of this patent is extended or adjusted under 35 U.S.C. 154(b) by 304 days.

(21) Appl. No.: 15/116,998

(22) PCT Filed: Feb. 14, 2014

(86) PCT No.: PCT/US2014/016595
§ 371 (c)(1),
(2) Date: Aug. 5, 2016

(87) PCT Pub. No.: WO2015/122921
PCT Pub. Date: Aug. 20, 2015

(65) Prior Publication Data
US 2017/0165435 A1    Jun. 15, 2017

(51) Int. Cl.
*A61M 5/36* (2006.01)
*A61M 5/14* (2006.01)
*A61M 5/142* (2006.01)

(52) U.S. Cl.
CPC ............... *A61M 5/36* (2013.01); *A61M 5/14* (2013.01); *A61M 5/142* (2013.01)

(58) Field of Classification Search
CPC ...... A61M 1/3627; A61M 5/14; A61M 5/142; A61M 5/36
See application file for complete search history.

(56) References Cited

U.S. PATENT DOCUMENTS 3,610,230 A    10/1971    Andersen
4,344,777 A *  8/1982    Siposs ................. A61M 1/3627
                                                      210/436
(Continued)

FOREIGN PATENT DOCUMENTS

CN    301729330 S    11/2011
CN    301729332 S    11/2011
(Continued)

OTHER PUBLICATIONS

U.S. Office Action dated Sep. 30, 2016, from related U.S. Appl. No. 29/545,199.
(Continued)

*Primary Examiner* — Laura A Bouchelle
(74) *Attorney, Agent, or Firm* — Steve Hassid; Partners Law Group, Inc.

(57) ABSTRACT

An air removal device for an intravenous fluid system includes a housing with an inlet for fluid communication with a fluid source, a fluid outlet for fluid communication with a blood vessel of a patient, and an air outlet. The air removal device further includes a disrupting element disposed within the housing in a flow path between the inlet and the fluid outlet, and an air chamber in fluid communication with the air outlet. The disrupting element includes a protrusion extending across the flow path. The flow path includes a first cross-sectional flow area at the inlet, and a second cross-sectional flow area at the protrusion. The second cross-sectional flow area is smaller than the first cross-sectional flow area.

18 Claims, 7 Drawing Sheets

(56) References Cited

U.S. PATENT DOCUMENTS

| | | | |
|---|---|---|---|
| 4,365,630 | A | 12/1982 | McFarlane |
| D282,204 | S | 1/1986 | Holt |
| D304,079 | S | 10/1989 | McFarlane |
| D323,889 | S | 2/1992 | Wyatt et al. |
| D338,955 | S | 8/1993 | Gresl et al. |
| D339,189 | S | 9/1993 | Nilsson |
| 5,284,486 | A | 2/1994 | Kotula et al. |
| D363,702 | S | 10/1995 | McFadden |
| D370,063 | S | 5/1996 | Spreckelmeier |
| D372,311 | S | 7/1996 | Koros et al. |
| D376,645 | S | 12/1996 | Lindgren et al. |
| 5,779,674 | A | 7/1998 | Ford |
| 6,053,899 | A | 4/2000 | Slanda et al. |
| D446,865 | S | 8/2001 | Conway |
| D449,104 | S | 10/2001 | Baker et al. |
| 6,315,755 | B1 | 11/2001 | Sussman |
| D452,004 | S | 12/2001 | Baker et al. |
| D457,955 | S | 5/2002 | Bilitz |
| D458,134 | S | 6/2002 | Berish et al. |
| D461,555 | S | 8/2002 | Binet et al. |
| 6,508,859 | B1 | 1/2003 | Zia et al. |
| 6,595,943 | B1 | 7/2003 | Burbank |
| D482,121 | S | 11/2003 | Harding et al. |
| D482,447 | S | 11/2003 | Harding et al. |
| 6,716,189 | B1 | 4/2004 | Jarvik et al. |
| D495,417 | S | 8/2004 | Doelling et al. |
| 7,018,360 | B2 | 3/2006 | Flaherty et al. |
| D520,041 | S | 5/2006 | Wheat |
| D522,595 | S | 6/2006 | Donahue et al. |
| 7,097,690 | B2 | 8/2006 | Usher et al. |
| 7,410,248 | B2 | 8/2008 | Umeda et al. |
| D586,913 | S | 2/2009 | Leroy et al. |
| D593,801 | S | 6/2009 | Wilson et al. |
| 7,569,029 | B2 | 8/2009 | Clark |
| D600,793 | S | 9/2009 | Bierman et al. |
| D612,050 | S | 3/2010 | Baynham |
| 7,896,832 | B2 | 3/2011 | Zafirelis et al. |
| D642,548 | S | 8/2011 | Bowen, III |
| D647,496 | S | 10/2011 | Tung |
| 8,029,728 | B2 | 10/2011 | Lindsay |
| 8,062,270 | B2 | 11/2011 | Sweeney |
| D657,867 | S | 4/2012 | Effenberger |
| 8,211,047 | B2 | 7/2012 | Cerasoli et al. |
| D667,546 | S | 9/2012 | Becker |
| 8,313,954 | B2 | 11/2012 | Leach et al. |
| D672,238 | S | 12/2012 | Aziz et al. |
| D673,673 | S | 1/2013 | Wang |
| D674,479 | S | 1/2013 | Merchant et al. |
| 8,393,328 | B2 | 3/2013 | Angel et al. |
| 8,394,052 | B2 | 3/2013 | Jessop et al. |
| 8,574,219 | B2 | 11/2013 | Adams et al. |
| 8,632,624 | B2 | 1/2014 | Cassidy et al. |
| D715,423 | S | 10/2014 | Rogers |
| D715,921 | S | 10/2014 | Wan |
| D720,850 | S | 1/2015 | Hsia et al. |
| D722,160 | S | 2/2015 | Armstrong |
| D727,499 | S | 4/2015 | Schad et al. |
| D733,291 | S | 6/2015 | Wang |
| D741,476 | S | 10/2015 | Hiraoka et al. |
| D748,253 | S | 1/2016 | Ratjen et al. |
| D751,691 | S | 3/2016 | Shaw et al. |
| D753,283 | S | 4/2016 | Efinger |
| D758,579 | S | 6/2016 | Keckstein et al. |
| D761,961 | S | 7/2016 | Tan et al. |
| D768,868 | S | 10/2016 | Inoue |
| D773,664 | S | 12/2016 | Deneui |
| D774,181 | S | 12/2016 | Green |
| D782,026 | S | 3/2017 | Bresco Torras et al. |
| 2011/0118704 | A1 | 5/2011 | Riaz |
| 2013/0092640 | A1 | 4/2013 | Cassidy et al. |
| 2015/0343157 | A1 | 12/2015 | Basile et al. |
| 2016/0067391 | A1 | 3/2016 | Real et al. |
| 2016/0129220 | A1 | 5/2016 | Jagadeesan et al. |

FOREIGN PATENT DOCUMENTS

| | | |
|---|---|---|
| CN | 301978850 S | 7/2012 |
| EM | 003359108-0001 | 8/2016 |
| EM | 003359108-0002 | 8/2016 |
| EP | 2 497 512 | 9/2012 |
| GB | 2 039 434 | 6/1994 |
| JP | 05-058151 | 8/1993 |
| JP | 2007-508061 A | 4/2007 |
| SU | 1134199 | 1/1985 |
| SU | 1215718 | 3/1986 |
| WO | WO-2006/083220 A1 | 8/2006 |
| WO | WO-2012/128816 | 9/2012 |
| WO | WO-2013/099946 A1 | 7/2013 |

OTHER PUBLICATIONS

PCT International Search Report and Written Opinion dated Nov. 6, 2014, from related application No. PCT/US2014/016595.
U.S. Notice of Allowance dated Jul. 16, 2014, from related U.S. Appl. No. 29/456,396.
BD A-Line Syringe Without Needle 3ml Slip Tip, https://online.ebos.co.nz/default.cfm?action=displayproduct&product_code=21120424, 1 page.
BD SAF-T-Intima Closed IV Catheter System, http://www.bd.com/infusion/products/ivcatheters/sti.asp, 2 pages.
Extracorporeal Membrane Oxygenation,an Anesthesiologist's Perspective: Physiology and Principles, http://annals.in/article.asp?issn=0971-9784;year=2011;volume=14;issue=3;spage=218;epage=229;aulast=Chauhan;type=3.
IV Gravity Sets, https://sentramedical.co.uk/portfolio-view/iv-gravity-sets/, 2 pages.
Latex Short Type Y Injection Port for I.V. Tube, http://eastmed01.en.made-in-china.com/product/PqcQUOKAXdpz/China-Latex-Short-Type-YInjection-Port-for-I-V-Tube.html, 3 pages.
Pen Type IV Cannula Without Valve and Without Wings With CE&ISO Approval, http://sell.lulusoso.com/selling-leads/1215085/Y-type-I-V-Cannula-Types-of-cannula.html, 7 pages.
SAF-T-Intima Intravenous Cannula, http://www.clhgroup.co.uk/products/saf-t-intima-intravenous-cannula/3331/, 1 page.
Starting Intravenous Lines, http://www.mrprotocols.com/sset/iv.html, 5 pages.
U.S. Office Action dated Jun. 29, 2017, from U.S. Appl. No. 29/556,546.
U.S. Office Action dated Jun. 30, 2017, from U.S. Appl. No. 29/596,365.
Canadian Examiner's Report dated Dec. 19, 2016, from related application No. 170250.
Japanese Office Action dated Jan. 10, 2017, from related application No. 2016-18812.
Japanese Office Action dated Jan. 10, 2017, from related application No. 2016-18813.
Extended European Search Report dated Aug. 31, 2017, from application No. 14882436.0.
Japanese Office Action dated Sep. 19, 2017, from application No. 2016-552330.
U.S. Office Action dated Aug. 31, 2017, from U.S. Appl. No. 29/536,128.
U.S. Notice of Allowance dated Oct. 18, 2017, from U.S. Appl. No. 29/536,128.
International Preliminary Report on Patentability dated Aug. 25, 2016, from related international application No. PCT/US2014/016595.
U.S. Notice of Allowance dated Oct. 28, 2016, from U.S. Appl. No. 29/545,199.
Canadian Examiner's Report dated Mar. 28, 2017, from related application No. 170250.

* cited by examiner

GAS REMOVAL SYSTEMS AND METHODS

BACKGROUND

Embodiments relate generally to the field of fluid delivery systems. More specifically, the embodiments relate to an apparatus and method for removing air bubbles or another gas from a fluid delivery system.

An air embolism can occur when an air bubble or embolus becomes trapped in a blood vessel or in the heart and obstructs the normal flow of blood through the blood vessel (e.g., a vascular air embolus (VAE)) or the heart. Air in a patient's veins can travel to the right side of the heart and from the heart to the lungs. Air trapped in vessels providing blood to the lungs can inhibit pulmonary circulation and cause chest pain and rapid breathing. In some patients, the air may pass to the left side of the heart and on to the brain or the coronary arteries, which can lead to more serious complications. The effect of an air embolism is directly related to the size of the embolus and the rate of entry of the air into the blood vessel. 50 ml of air cause hypotension and dysrhythmias, while 300 ml can cause death if introduced rapidly, generally due to circulatory obstruction and cardiovascular collapse.

Air can become introduced in the blood vessels during surgery or another medical procedure, such as from a syringe. Air may be introduced in the form of bubbles trapped in a fluid introduced into the blood vessel (e.g., a blood transfusion, an intravenous (IV) fluid line supplying a fluid such as a saline solution or medicine). Small air bubbles may be present in the fluid as supplied. Additional air bubbles may be formed, for example, when priming the IV line if a roller clamp is released too quickly when priming the line.

A pump may be used to control the rate at which the fluids are introduced. Such pumps may include a system to detect when air is in the IV line. If an air bubble reaches the pump, an alarm may sound to alert the nursing staff or other caregiver and the pump turns off. The caregiver then must go to the patient, attempt to remove the air bubbles from the IV line. Every health care facility may have a specific protocol for this procedure, but it may involve low-tech and/or time consuming solutions such as "flicking" the IV bag and/or IV line to try and release the bubbles and get them to collect at the top of the bag, away from outlet.

Hundreds of millions of dollars and many hours of labor are spent by the nursing staff or other caregivers to initially prime the IV line, reset the pump alarm when it goes off, and purge air from the IV line. Additionally, the alarm built into the pump is a disturbance to the patient, as it is likely to wake the patient every time it goes off.

SUMMARY

One embodiment of the invention relates to an air removal device for an intravenous fluid system. The air removal device includes a housing with an inlet for fluid communication with a fluid source, a fluid outlet for fluid communication with a blood vessel of a patient, and an air outlet. The air removal device further includes a disrupting element disposed within the housing in a flow path between the inlet and the fluid outlet, and an air chamber in fluid communication with the air outlet. The disrupting element includes a protrusion extending across the flow path. The flow path includes a first cross-sectional flow area at the inlet, and a second cross-sectional flow area at the protrusion. The second cross-sectional flow area is smaller than the first cross-sectional flow area.

Another embodiment relates to an intravenous fluid system. The intravenous fluid system includes an inlet through which a fluid may enter the intravenous fluid system from a fluid bag, an outlet through which the fluid may be dispensed into a blood vessel of a patient, a passage through which a fluid may pass from the inlet to the outlet, and an air removal device disposed in between the inlet and the outlet. The air removal device includes a housing defining a flow path for the fluid, a disrupting element disposed within the housing, and an air chamber in fluid communication with the housing. The disrupting element includes a protrusion extending across the flow path. The flow path includes a first cross-sectional flow area defined by the housing, and a second cross-sectional flow area defined between the protrusion and the housing. The second cross-sectional flow area is smaller than the first cross-sectional flow area. The air removal device is positioned between the inlet and the outlet to prevent air in the passage from passing beyond the air removal device.

Another embodiment relates to a method for removing air from a fluid in an intravenous fluid system. The method includes providing an intravenous fluid system for use with a fluid bag containing a fluid. The intravenous fluid system includes an inlet, an outlet, a passage through which a fluid may pass from the inlet to the outlet, and an air removal device disposed between the inlet and the outlet. The air removal device is configured to passively remove air from the fluid and includes an air chamber with a variable internal volume. The method further includes preventing the flow of fluid through the passage with a clamping device, inserting the inlet into the fluid bag such that the passage is in fluid communication with the interior of the fluid bag, and releasing the clamp to allow fluid to enter the passage until the fluid reaches the outlet, passing through the air removal device. The method further includes preventing the flow of fluid through the passage with the clamping device, increasing the internal volume of the air chamber; and releasing the clamp to allow fluid to flow through the passage.

BRIEF DESCRIPTION OF THE DRAWINGS

Features, aspects, and advantages of the embodiments will become apparent from the following description, appended claims, and the accompanying exemplary embodiments shown in the drawings, which are briefly described below.

DETAILED DESCRIPTION

It is to be understood that the following detailed description is exemplary and explanatory only, and is not restrictive of the embodiments as claimed.

Figure 1:
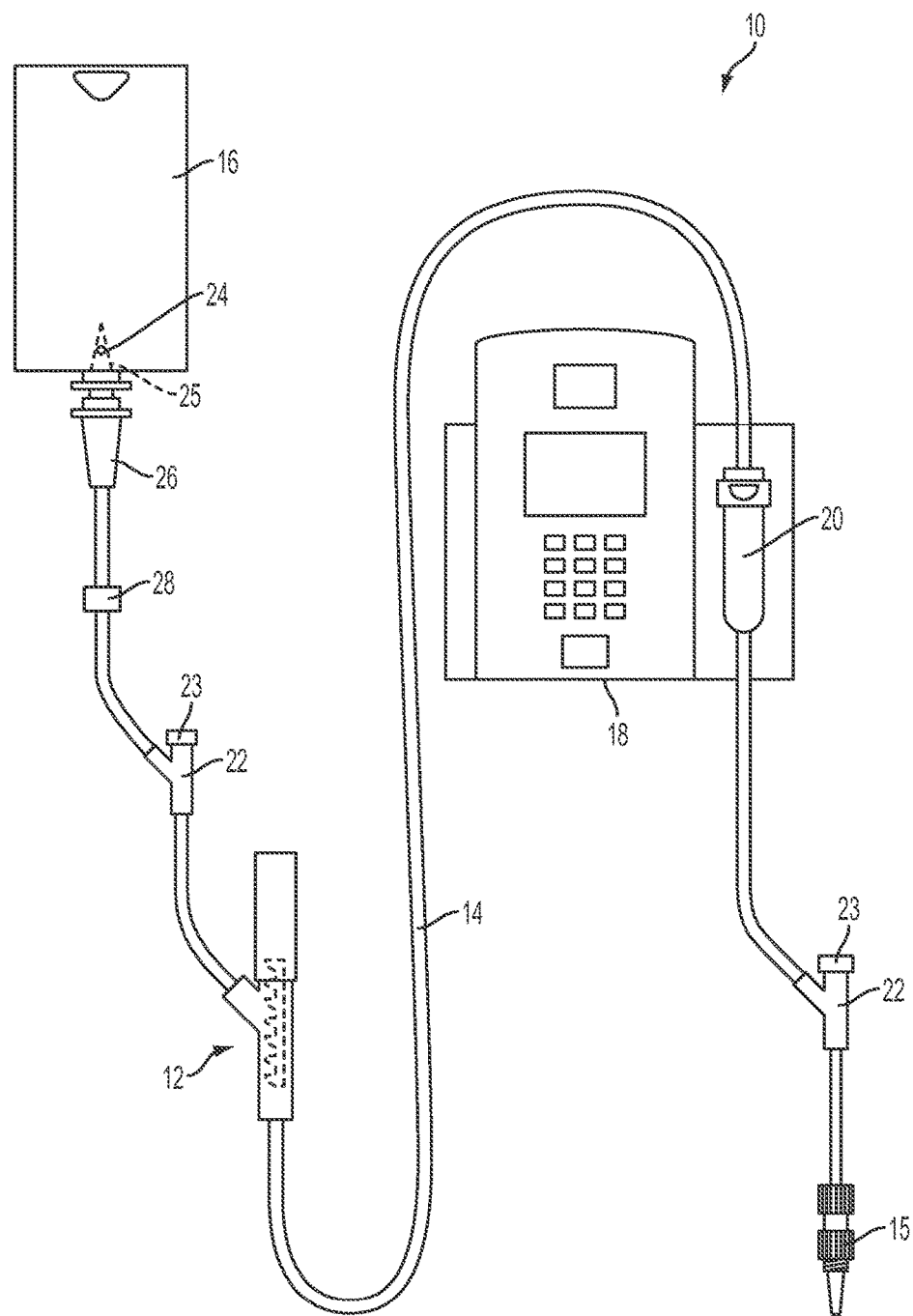
FIG. 1 is a schematic view of a fluid delivery apparatus including an air-removal apparatus, according to an exemplary embodiment.

Referring to FIG. 1, a fluid delivery system 10 is shown according to an exemplary embodiment to include an air removal device 12 (e.g., air catch, degasser, etc.). The fluid delivery system 10 is configured to transport a fluid from a fluid source, shown as a flexible intravenous (IV) bag 16, to a patient through generally closed passage, such as a passage provided by a length of tubing 14. In other embodiments, the fluid may be supplied from another source, such as a bottle or other closed, sterile container. The fluid delivery system 10 may be used to deliver a variety of fluids to the blood vessel of a patient including, but not limited to, volume expanders (e.g., a saline solution (NaCl) as fluid replacement to fight dehydration, a glucose solution etc.), whole blood (e.g., a blood transfusion), blood components (e.g., red blood cells, plasma, platelets, etc.), or medicine (e.g., chemotherapy medicine, antibiotics, etc.).

The fluid delivery system 10 may be coupled via an appropriate outlet connector 15 to a catheter inserted through the skin and into a vein. The vein may be a peripheral vein (e.g., a vein in an arm or leg) or a central vein (e.g., a vein in the head or chest). In other embodiments, the fluid delivery system 10 may deliver fluids into the body of the patient through another device, such as a port implanted in the skin of the patient. The outlet connector 15 may be, for example, a male Luer connector that is permanently coupled to the outlet of the fluid delivery system 10 (e.g., fused via heat or adhesive) and configured to be coupled to a corresponding female Luer connectors. In other embodiments, the outlet of the fluid delivery system 10 may be coupled to the catheter or another device with another type of connector (e.g., via a screw-type or pressure fitting, etc.).

In one embodiment, the flow rate of the fluid through the fluid delivery system 10 and into the blood vessel of the patient is monitored and controlled by a device, shown in FIG. 1 as an infusion pump 18. The infusion pump 18 may deliver the fluid at a constant rate, or intermittently, either at a frequency determined by a caregiver or directly by the patient. A portion of the fluid delivery system 10 passes through the infusion pump 18 and directly interfaces with the infusion pump 18 to control the flow rate of the fluid. In one embodiment, the fluid delivery system 10 includes a cassette 20 that is configured to fit into a corresponding socket of the infusion pump 18. In other embodiments, the fluid delivery system 10 may lack a cassette 20 and the infusion pump 18 may be configured to receive a length of the tubing 14.

In other embodiments, an infusion pump 18 may not be used and the fluid delivery system 10 may be a gravity drip system in which the IV bag 16 is suspended above the patient and the fluid is delivered via gravity. In other embodiments, two or more fluid delivery systems 10 may deliver fluids to a patient through a single catheter or other entry point. In such embodiments, one or more of the fluid delivery systems 10 may use an infusion pump to control the flow rate while one or more other fluid delivery systems 10 may be gravity feed systems.

The air removal device 12 removes air bubbles from the fluid delivery system 10 before the air bubbles reach the patient. By reducing the amount of air introduced into the blood vessel of the patient, the likelihood of complications related to air in the blood vessels, such as an air embolus causing an embolism, is reduced.

Some infusion pumps 18 may include a system to detect the presence of predetermined amount of air in the portion of the fluid delivery system 10 passing through the infusion pump 18. Such an air-in-line detection system may be configured to take precautionary measures, such as halting the flow of fluid through the fluid delivery system 10, and/or alerting the caregiver. The alert may be, for example, an audio tone that is activated when air is detected and continues until the air is removed from the fluid delivery system 10 and the infusion pump 18 is reset. If positioned in the fluid delivery system 10 upstream from an infusion pump 18, the air removal device 12 reduces the occurrences of these alerts, which reduces the disturbances of both the patient and the caregiver.

Referring still to FIG. 1, fluid enters the fluid delivery system 10 through an inlet, shown as an opening 24 in a spike 25 configured to pierce the IV bag 16. The spike 25 is coupled to a drip chamber 26 suspended below the IV bag 16. The fluid drips or otherwise flows out of the IV bag 16, through the opening 24, and into the drip chamber 26 at a controlled rate. The size of the opening 24 may be chosen to achieve a desired drop size and rate. When the fluid delivery system 10 is primed (i.e., generally filled with fluid) and in use, the drip chamber 26 is generally only partially filled with fluid. The fluid passes from the drip chamber 26 to the remainder of the fluid delivery system 10 while much of the air remains in the drip chamber 26 or flows back into the IV bag 16 through the opening 24. However, some air may pass with the fluid from the drip chamber 26 to the remainder of the fluid delivery system 10.

From the drip chamber 26, the fluid may pass via the tubing 14 through other components, such as a check valve 28 and a connector, shown as forked tube or y-site 22. One fluid delivery system 10 (e.g., a secondary set, piggyback set, etc.) may join or "piggyback" another fluid delivery system 10 (e.g., a primary set) via the y-site 22. The y-site 22 is a junction that includes a port 23 (e.g., med port, injection port, etc.) which allows another substance to be introduced into the fluid delivery system 10. The substance may be, for example, a second fluid from a second fluid source. The second fluid may be delivered from a fluid source similar to the IV bag 16 via tubing that interfaces with the y-site 22, from a syringe with a needle that pierces the port 23, or from a syringe that interfaces with the y-site 22 in another way, such as with a connector (e.g., a Luer connector or another needleless connector). The two fluid delivery systems 10 may each run continuously, one fluid delivery system 10 may run continuously while the other fluid delivery system 10 periodically adds the second fluid to the first fluid, or the first fluid delivery system 10 may halt when the second fluid delivery system 10 is active. The introduction of a second fluid into the fluid delivery system 10 may introduce additional air into the system.

Figure 2:
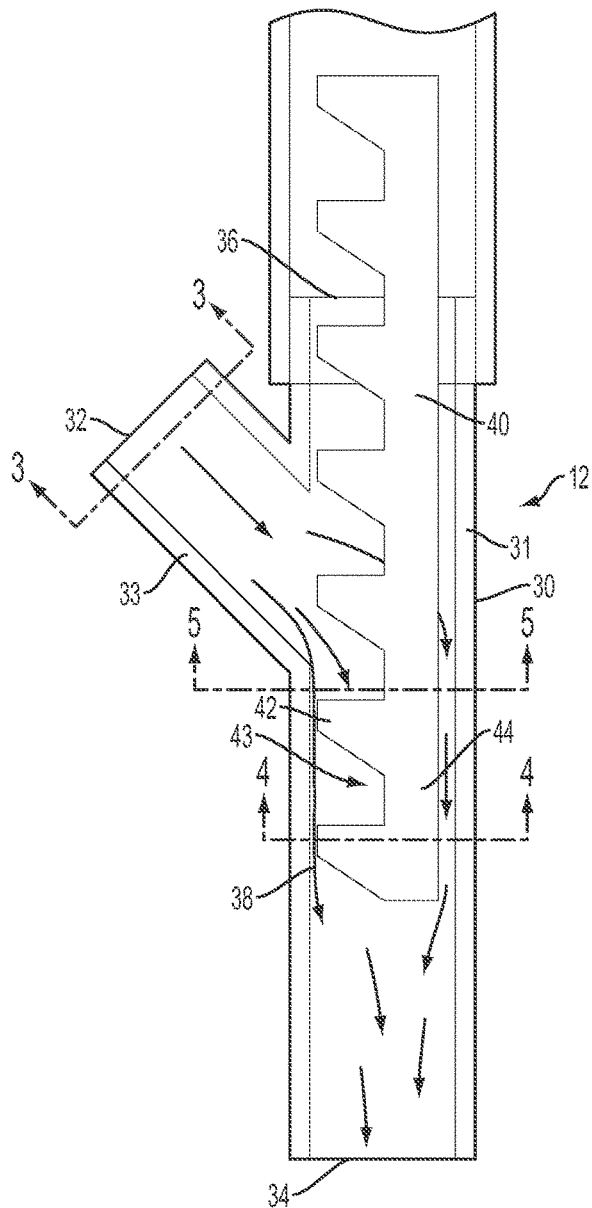
FIG. 2 is a schematic view of an air-removal apparatus, according to an exemplary embodiment.

Referring now to FIG. 2, an air removal device 12 is shown according to an exemplary embodiment. The air removal device 12 is positioned along the fluid path between the inlet and the outlet of the fluid delivery system 10 (e.g., joined to tubing 14 through which the fluid flows from the opening 24 to the outlet connector 15). The air removal device 12 includes a housing 30 defining an inlet 32, a fluid outlet 34, an air outlet 36, and a flow path 38 along which fluid passes through the housing 30 from the inlet 32 to the fluid outlet 34. According to an exemplary embodiment, the housing 30 is formed of a rigid, FDA-approved material. In one embodiment, the housing 30 is generally formed as a main cylindrical portion 31 and an angled cylindrical portion 33 that intersects with the main cylindrical portion 31. The fluid outlet 34 and the air outlet 36 are provided on opposite ends of the main cylindrical portion 31 and the inlet 32 is provided at the distal end of the angled cylindrical portion 33. The arrangement of the outlets 34 and 36 on opposite ends of the housing facilitates the removal of air from the fluid flow path 38.

The cylindrical portions 31 and 33 have inner diameters that are configured to receive the tubing 14, such as a standard ¼" diameter polymer (e.g., polypropylene, nylon, etc.) tubing. In other embodiments, the cylindrical portions 31 and 33 may be sized to receive tubing of another diameter. Tubing 14 is coupled to the inlet 32 and the outlet 34 with an appropriate water-tight coupling mechanism to form a sterile, closed passage from the tubing 14 coupled to the inlet 32, through the interior of the housing 30 along the flow path 38, to the tubing 14 coupled to the fluid outlet 34. The tubing 14 may be permanently coupled to the housing (e.g., by adhesive, by heat staking, etc.) or may be removably coupled to the housing, such as with a Luer connector or another appropriate screw-type or pressure fitting.

In other embodiments, the housing 30 may be otherwise shaped. For example, the interior of the housing 30 may be generally flattened, or may have a rectangular cross-section. In other embodiments, the inlet 32 and outlets 34 and 36 may be otherwise arranged relative to each other. For example, the housing 30 may be a T-shaped body.

A disrupting device, shown in FIG. 2 as an insert 40 is disposed within the housing 30 in the flow path 38. At least some of the air bubbles in the fluid passing along the flow path 38 are diverted such that they do not pass through the fluid outlet 34. Instead, the air passes through the air outlet 36 into a chamber 50 that is outside of the flow path 38.

According to an exemplary, the insert 40 is an elongated member that is formed from an FDA-approved material that does not react in the presence of the fluid. The insert 40 may be coupled to the interior of the housing 30, such as with an adhesive. In another embodiment, the insert 40 may not be coupled to the interior of the housing 30 and may be retained in the housing 30 by the internal geometry of the housing 30. In another embodiment, the insert 40 may be integrally formed with the housing 30 as a single body.

The insert 40 includes a multitude of protrusions 42 (e.g., ledges, flanges, baffles, ledges, etc.) extending from a main body 44. The protrusions 42 are separated by gaps or notches 43. The protrusions 42 include a face 46 orthogonal to the direction of the fluid flow. The face 46 obstructs the flow of the fluid through the housing 30 to inhibit the passage of air bubbles along the flow path 38. In other embodiments, the face 46 may not be orthogonal to the flow but instead may be inclined at an angle (e.g., in an upstream direction, in a downstream direction, etc.). While the face 46 is illustrated as a generally flat plane, in other embodiments, the face 46 may be otherwise shaped or contoured (e.g., concave, convex, corrugated, etc.). According to one exemplary embodiment, the insert 40 includes eight similarly sized and shaped protrusions 42 that are spaced generally evenly along the length of the insert 40. In another embodiment, the protrusions 42 may be unevenly distributed along the length of the insert 40. In another embodiment, the protrusions 42 may be shaped differently from one another to facilitate the removal of additional air from the fluid.

Figure 3:
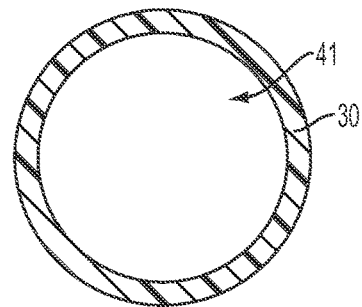
FIG. 3 is a cross section view of the air-removal apparatus of FIG. 2, taken along line 3-3.
Figure 4:
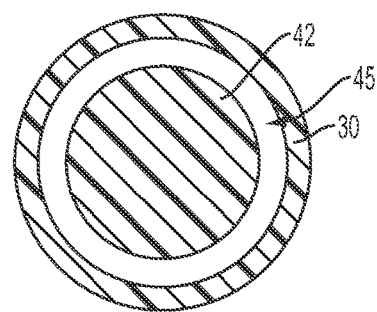
FIG. 4 is a cross section view of the air-removal apparatus of FIG. 2, taken along line 4-4.
Figure 5:
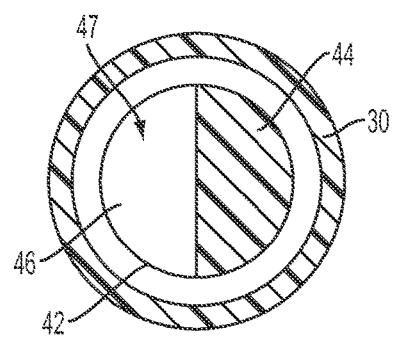
FIG. 5 is a cross section view of the air-removal apparatus of FIG. 2, taken along line 5-5.

Referring to FIGS. 3-5 the cross-sectional area of the flow path 38 changes as it passes around the insert 40. The fluid enters the housing 30 at the inlet 32, which has a first cross-sectional area 41 defined by the internal diameter of the housing 30. At the protrusion 42, the face 46 obstructs the fluid flow, forcing the fluid to pass around the insert 40 into an annular space between the protrusion 42 and the housing 30 defining a second cross-sectional area 45. According to an exemplary embodiment, the second cross-sectional area 45 is less than approximately 50% of the first cross-sectional area 41. According to a preferred embodiment, the second cross-sectional area 45 is less than approximately 33% of the first cross-sectional area 41. The fluid continues to flow beyond the protrusion into an intermediate cavity formed by the gap 43. The intermediate cavity has a third cross-sectional area 47 that includes the annular space between the protrusion 42 and the housing 30 and the area between the main body 44 and the housing 30. The third cross-sectional area 47 is greater than the second cross-sectional area 45, but less than the first cross-sectional area 41.

The protrusions 42 and the varying cross-sectional flow areas along the flow path 38 disrupt the passage of air along the flow path 38. Large bubbles and volumes of air (e.g., having a diameter approximately equal to the inner diameter of the tubing 14) entering the air removal device 12 are broken up into smaller bubbles that float away from the flow path 38 and out of the housing 30 through the air outlet 36. Relatively small bubbles may be caught in the intermediate cavity formed by the gap 43 until they grow larger in diameter and float away from the flow path 38 and out of the housing 30 through the air outlet 36.

It is believed that the force from surface tension overcomes the internal pressure force of the bubble as the bubble passes through the restricted flow area around the protrusion 42. This reduced flow area collapses the bottom portion of the bubble and force the bubble to move upstream and not pass beyond the protrusion. When sufficient air gets trapped in place, either a relatively large bubble or a bubble formed in one of the gaps 43 from smaller bubbles, the pressure inside the bubble forces it up, away from the protrusion 42.

Figure 6A:
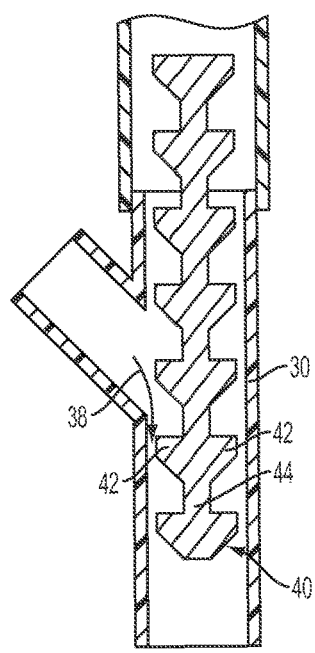
FIGS. 6A-D are schematic views of disrupters for an air-removal apparatus, according to several other exemplary embodiments.
Figure 6B:
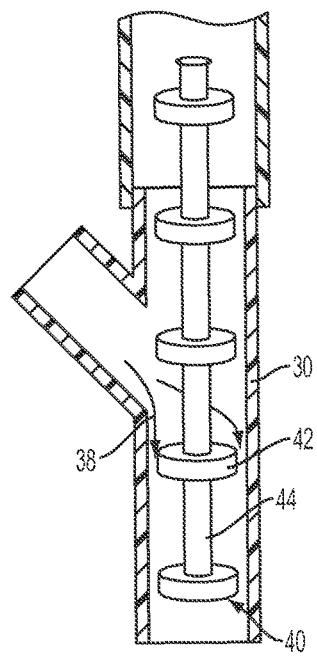
Figure 6C:
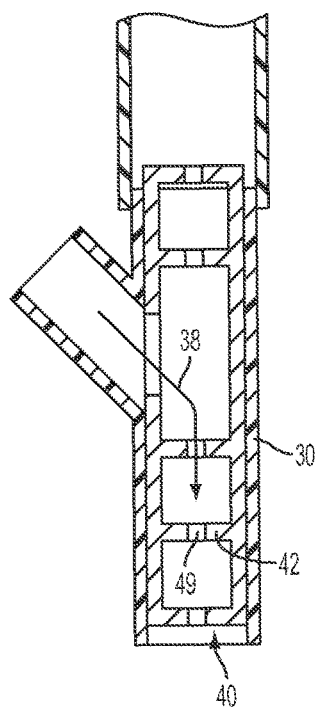
Figure 6D:
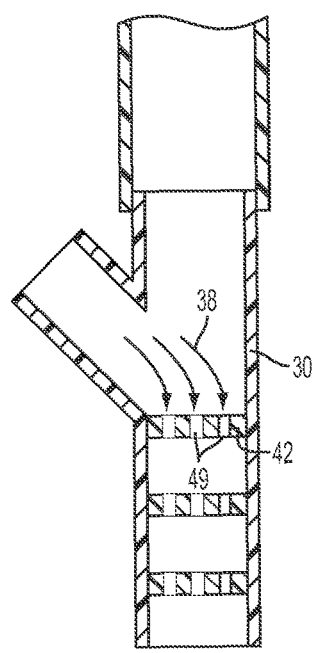

Referring now to FIGS. 6A-6D, several other embodiments of an insert are illustrated. As shown in FIG. 6A, in one embodiment the insert 40 may include protrusions 42 extending from multiple sides of the main body 44. As shown in FIG. 6B, in another embodiment the insert 40 may include protrusions 42 extending outward radially from the main body 44. As shown in FIG. 6C, in another embodiment the protrusions 42 may extend inwardly from the outer housing 30 and the flow path 38 may pass through an opening 49 in the protrusion 42 rather than through the annular space between the insert 40 and the housing 30. As shown in FIG. 6D, in another embodiment the protrusions 42 may be walls or plates extending across the interior of the housing and the flow path may pass through one or more openings 49 (e.g., holes, apertures, slots, etc.) in the protrusions 42.

Figure 7A:
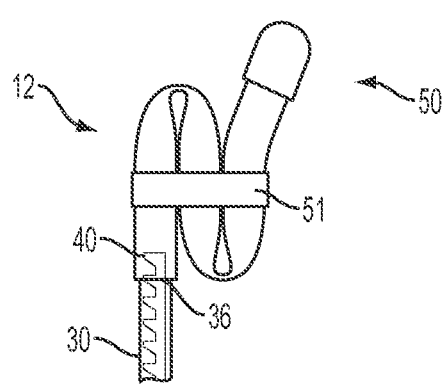
FIGS. 7A-7B are schematic views of an air chamber for an air-removal apparatus, according to various exemplary embodiment.
Figure 7B:
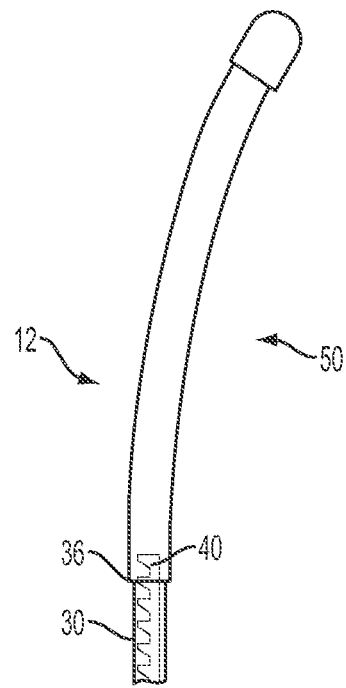

Referring now to FIGS. 7A-7B, the air chamber 50 is shown according to an exemplary embodiment. The air chamber 50 provides a cavity into which air is diverted from the fluid in the flow path 38 such that it does not continue through the fluid delivery system 10 downstream of the air removal device 12 (e.g., to the pump 18 or to the patient). The air chamber 50 is configured to have an internal volume that is sufficient to contain any air that would be typically be contained in a IV bag 16 as well as air that may be introduced into the fluid delivery system from other sources (e.g., a secondary line or a syringe via a y-site 22 or other connector.

In one embodiment, the air chamber 50 is a flexible, tubular body with a sealed end. The air chamber 50 is formed from an FDA-approved material that does not react in the presence of the fluid. The air chamber 50 may be formed, for example, from a suitable polymer (e.g., polypropylene, nylon, etc.). The air chamber 50 is coupled to the air outlet 36 of the housing 30 with an appropriate air-tight coupling mechanism to form a sterile, closed passage from the interior of the housing 30 to the interior of the air chamber 50. The end of the insert 40 may extend through the air outlet 36 into the interior of the air chamber 50.

The air chamber 50 may be configured to have a variable (e.g., expandable) internal volume. As shown in FIG. 7A, in a first or compressed configuration, the air chamber 50 is folded one or more times, reducing the internal volume of the air chamber 50. The air chamber 50 is retained in the compressed configuration with a removable device, shown as a length of tape 51 that is wrapped around the folded air chamber 50. In other embodiments, the air chamber 50 may be retained in the compressed configuration with another device, such as a clamp, cable tie, band, strap, a hook and loop strip, etc. The air chamber 50 can be converted to a second or expanded configuration to increase the internal volume of the air chamber 50. As shown in FIG. 7B, the elastic properties of the material forming the air chamber 50 will automatically expand the air chamber 50 if the tape 51 or other device is removed.

The air chamber 50 may be provided initially in the compressed configuration, such as a part of a fluid supply system 10 provided in a sealed package. After the fluid supply system 10 is coupled to the IV bag 16 by a caregiver, it may be primed by allowing the fluid from the bag 16 to flow through the fluid supply system until it reaches the outlet connector 15. Once the fluid supply system 10 is primed, the air chamber 50 may be converted to the expanded configuration. The expansion of the air chamber 50 draws fluid from the fluid supply system 10 (e.g., fluid in the housing 30 of the air removal device 12) through the air outlet 36 and into the interior of the air chamber 50, at least partially filling the air chamber 50 with fluid. Once the fluid supply system 10 is coupled to a patient and delivers fluid to the patient, air collected from the fluid can collect in the air chamber 50 and displace fluid from the air chamber 50.

Figure 8A:
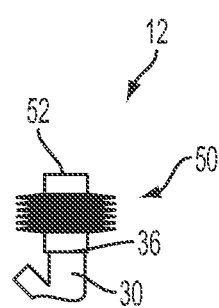
FIGS. 8A-8B are schematic views of an air chamber for an air-removal apparatus, according to another exemplary embodiment.
Figure 8B:
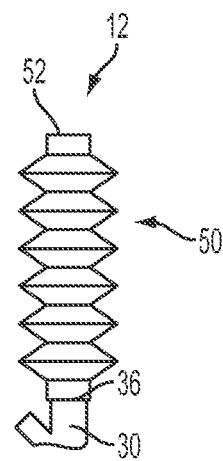

The internal volume of the air chamber 50 may be expanded in various ways. For example, in another embodiment shown in FIGS. 8A-8B, the air chamber 50 may have accordion pleated, expandable walls. In the compressed configuration, the end wall 52 of the air chamber 50 is pushed towards the housing 30. In the expanded configuration, the end wall 52 is pulled away from the housing 30.

Figure 9A:
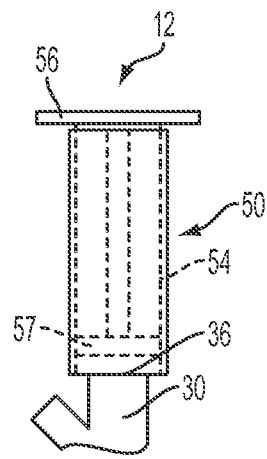
FIG. 9A-9B are schematic views of an air chamber for an air-removal apparatus, according to another exemplary embodiment.
Figure 9B:
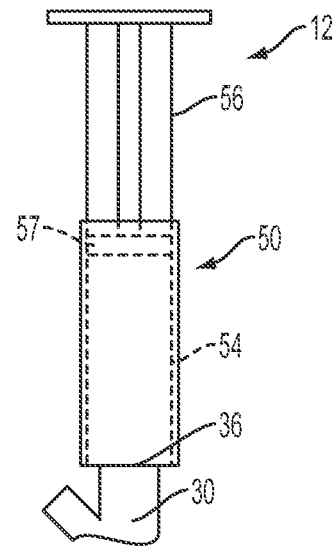

In other embodiments, the walls 54 of the air chamber 50 may be rigid and the internal volume of the air chamber 50 may be varied using another member. For example, in another embodiment shown in FIGS. 9A-9B, the air chamber 50 may include a cylindrical side wall 54 defining a bore and a plunger 56 moveable relative to the side wall 54. The head 57 of the plunger 56 engages the inside surface of the cylindrical wall with an air-tight interface. As the plunger 56 is drawn away from the housing 30, the internal volume of the air chamber 50, as partially defined by the head 57, increases.

Figure 10A:
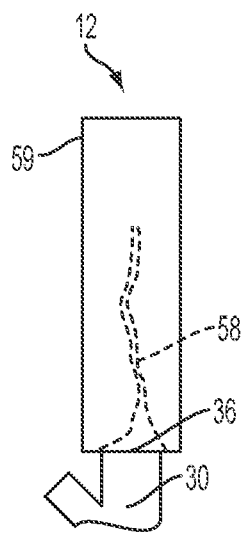
FIGS. 10A-10B are schematic views of an air chamber for an air-removal apparatus, according to another exemplary embodiment.
Figure 10B:
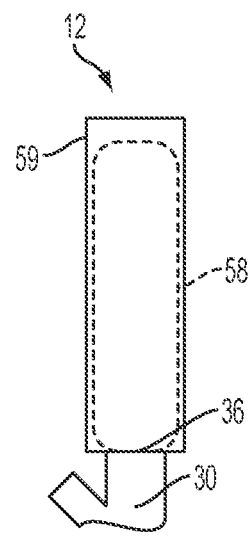

In other embodiments, a caregiver may not actively vary the volume of the air chamber 50 after priming the fluid supply system 10. For example, in another embodiment shown in FIGS. 10A and 10B, the air chamber 50 may include a flexible bladder 58. In the compressed configuration, the bladder 58 is uninflated. As air is removed from the fluid and enters the air chamber 50, the bladder 58 becomes inflated. The air chamber 50 may further include a rigid outer housing 59 to protect the bladder from damage or accidental compression. The outer housing 59 includes openings allowing the inflating bladder 58 to displace air out of the interior of the housing 59.

In another embodiment, the air may not be collected in the air chamber 50. Instead, air may exit the air outlet 36 and pass through a device such as a low pressure check valve to be released to the atmosphere. The check valve allows air to exit the fluid supply system 10 without allowing outside contaminants to enter the fluid supply system 10.

In still another embodiment, the air may not be collected in the air chamber but may be routed to another sealed body. For example, the air removal device 12 may include a return line coupled between the air outlet 36 and another chamber, such as the drip chamber 26 or the IV bag 16 (e.g., through a port in the upper portion of the IV bag 16, above the level of the fluid contained therein).

Air may be effectively removed from the fluid with the air removal device 12 even if the air does not enter the air chamber 50. For example, air bubbles trapped by the insert 40 in the intermediate chambers formed by the gaps 43 are prevented from continuing with the fluid to be expelled out of the outlet connector 15 and into the patient's blood vessel. Similarly, air may displace fluid not only from the interior of the air chamber 50 as described above, but also from the upper portion of the housing 30 (e.g., the portion of the main cylindrical portion 31 proximate the air outlet 36) outside of the flow path 38 without interrupting the flow of fluid through the fluid delivery system 10.

Figure 11:
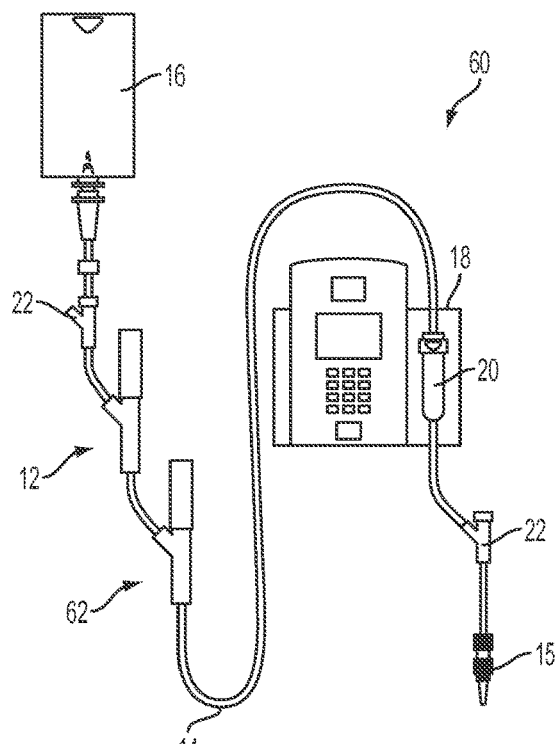
FIG. 11 is a schematic view of a fluid delivery apparatus including an air-removal apparatus, according to another exemplary embodiment.

Referring now to FIG. 11, a fluid delivery system 60 is shown according to another exemplary embodiment. The fluid delivery system 60 is configured similar to the fluid system 10 described above. The fluid delivery system 60 includes an additional air removal device 62 in series with the air removal device 12. Both air removal devices 12 and 62 are provided upstream from the cassette 20. The second air removal device 62 is positioned downstream from the first air removal device 12 such that an inlet of the second air removal device 62 is coupled to the fluid outlet 34 of the first air removal device 12. The second air removal device 62 is therefore positioned to capture any air that is able to pass the first air removal device 12 and divert it away from the fluid continuing to the cassette 20, thereby reducing the likelihood that air will reach the cassette 20 and trigger an alarm by the pump 18.

Figure 12:
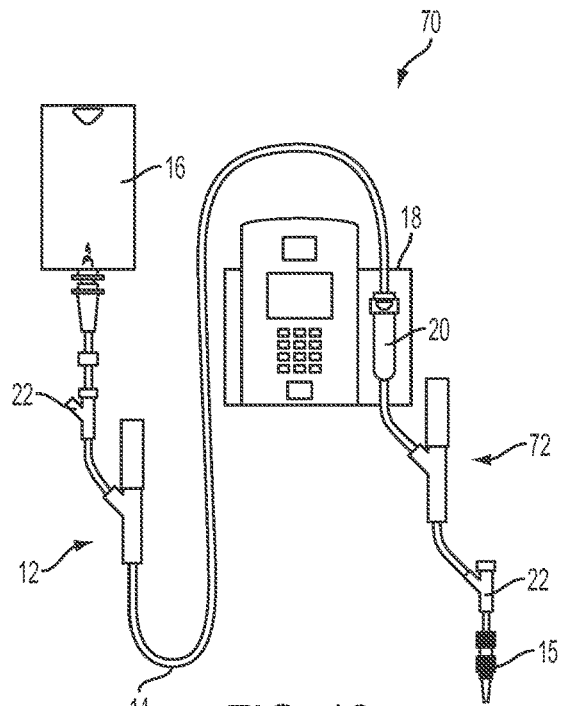
FIG. 12 is a schematic view of a fluid delivery apparatus including an air-removal apparatus, according to another exemplary embodiment.

Referring now to FIG. 12, a fluid delivery system 70 is shown according to another exemplary embodiment. The fluid delivery system 70 is configured similar to the fluid system 10 described above. The fluid delivery system 70 includes an additional air removal device 72 in series with the air removal device 12. The air removal device 72 is provided downstream from the cassette 20. Some very small bubbles may be able to pass the first air removal device 12. Such small bubbles may also be able to pass through the pump 18 without triggering the alarm. While such small bubbles may be sufficiently decreased in size such that they have a negligible effect on an adult, they may still have an adverse on a small child, such as a small child in a neonatal intensive care unit. According to an exemplary embodiment, the second air removal device 72 may be configured to capture small bubbles that are able to pass the first air removal device 12. The second air removal device 72 is therefore positioned and configured to capture any air that is able to pass the first air removal device 12 and divert it away from fluid flow to the outlet connector 15, thereby reducing the likelihood that air will reach the patient.

Figure 13:
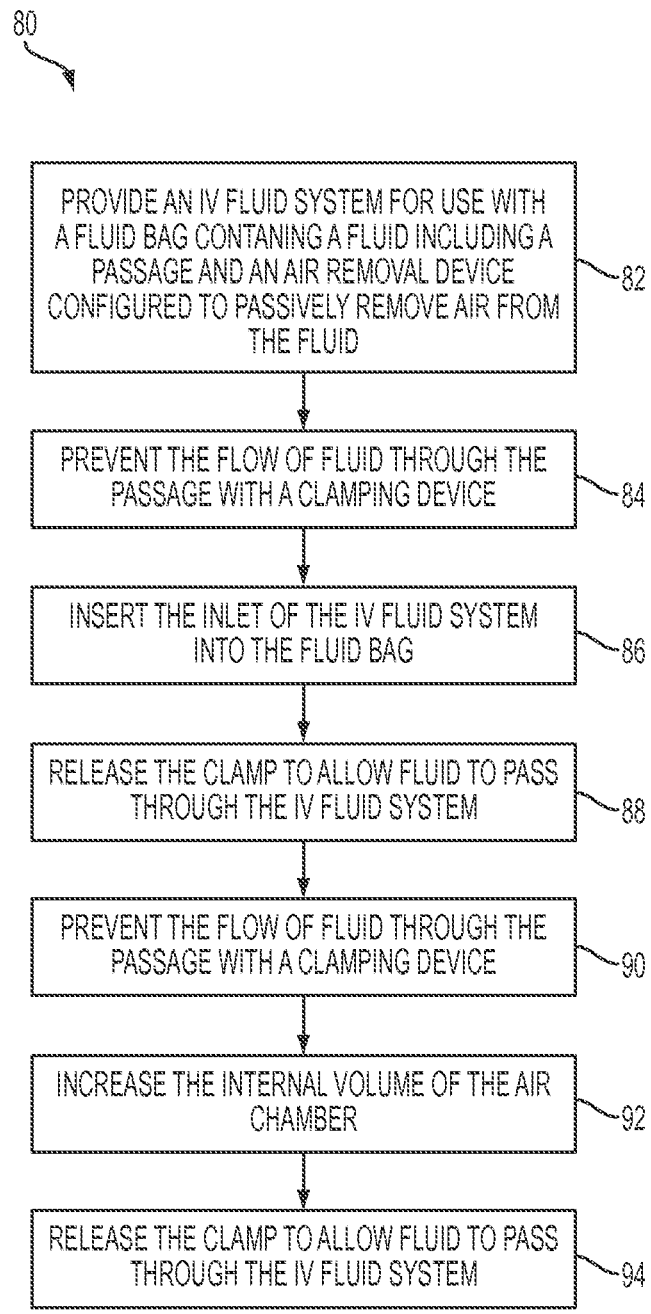
FIG. 13 is a flowchart of a method for removing air from a fluid in an intravenous fluid system, according to an exemplary embodiment.

Referring now to FIG. 13, a flowchart of a method 80 for removing air from a fluid in an intravenous fluid system is shown according to an exemplary embodiment. An intravenous fluid system for use with a fluid bag containing a fluid is provided (step 82). The intravenous fluid system includes an inlet, an outlet, a passage through which a fluid may pass from the inlet to the outlet, and an air removal device disposed between the inlet and the outlet. The air removal device is configured to passively remove air from the fluid and includes an air chamber with a variable internal volume. Flow of fluid through the passage is prevented using a clamping device (step 84). The flow may be prevented or adjusted, for example, using a clamp coupled to the tubing 14. The clamp may be a roller clamp, slide clamp, pinch clamp, or any other mechanism that is configured to partially or completely close the internal passage through the tubing 14 by pinching, bending, or otherwise distorting the tubing 14. The inlet is inserted into the fluid bag such that the passage is in fluid communication with the interior of the fluid bag (step 86). The clamp is released to allow fluid to enter the passage. The fluid flows through the passage until the fluid reaches the outlet, passing through the air removal device (step 88). The clamp is generally released rather slowly to minimize the amount of air bubbles that enter the passage. Once the fluid has reached the outlet, the flow of fluid through the passage is prevented with the clamping device (step 90). The internal volume of the air chamber is increased, drawing fluid into the air chamber (step 92). The clamp is then released to allow fluid to flow through the passage such that the air removal device removes air from the fluid (step 94).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The construction and arrangement of the elements of the IV line air removal device as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations.

What is claimed is:

1. An air removal device for an intravenous fluid system, comprising:
    a housing comprising:
        an inlet for fluid communication with a fluid source;
        a fluid outlet for fluid communication with a blood vessel of a patient; and
        an air outlet;
    a disrupting element disposed within the housing in a flow path between the inlet and the fluid outlet, comprising a protrusion extending across the flow path; and
    an air chamber in fluid communication with the air outlet;
    wherein the flow path comprises a first cross-sectional flow area at the inlet, and a second cross-sectional flow area at the protrusion, the second cross-sectional flow area being smaller than the first cross-sectional flow area;
    wherein the disrupting element further comprises a main body extending in the direction of the flow path, the flow path comprising a third cross-sectional flow area at the main body, and wherein the third cross-sectional flow area is greater than the second cross-sectional flow area and smaller than the first cross-sectional flow area.

2. The air removal device of claim 1, wherein the second cross-sectional flow area is less than 33% of the first cross-sectional area.

3. The air removal device of claim 1, wherein the disrupting element comprises a plurality of protrusions spaced along the main body.

4. The air removal device of claim 3, wherein the disrupting element extends through the air outlet into the air chamber.

5. The air removal device of claim 4, wherein the air outlet and the air chamber are positioned upstream from the fluid outlet.

6. The air removal device of claim 1, wherein the air chamber comprises a variable internal volume.

7. The air removal device of claim 6, wherein the air chamber comprises a flexible sidewall.

8. The air removal device of claim 6, wherein the air chamber comprises a collapsible accordion sidewall.

9. The air removal device of claim 6, wherein the air chamber comprises a flexible bladder.

10. An intravenous fluid system, comprising:
an inlet through which a fluid may enter the intravenous fluid system from a fluid bag;
an outlet through which the fluid may be dispensed into a blood vessel of a patient;
a passage through which a fluid may pass from the inlet to the outlet; and
an air removal device disposed between the inlet and the outlet, comprising:
a housing defining a flow path for the fluid,
a disrupting element disposed within the housing, comprising a protrusion extending across the flow path; and
an air chamber in fluid communication with the housing;
wherein the flow path comprises a first cross-sectional flow area defined by the housing, and a second cross-sectional flow area defined between the protrusion and the housing, the second cross-sectional flow area being smaller than the first cross-sectional flow area;
an insertable portion disposed between the air removal device and the outlet, the insertable portion configured to be inserted into a pump, the pump configured to draw a fluid through the passage;
wherein the air removal device is positioned between the inlet and the outlet to prevent air in the passage from passing beyond the air removal device.

11. The intravenous fluid system of claim 10, wherein the second cross-sectional flow area is less than 33% of the first cross-sectional area.

12. The intravenous fluid system of claim 11, further including a second air removal device disposed between the inlet and the insertable portion.

13. The intravenous fluid system of claim 11, further including a second air removal device disposed between the insertable portion and the outlet.

14. The intravenous fluid system of claim 11, wherein the insertable portion comprises a cassette configured to interface with the pump.

15. A method for removing air from a fluid in an intravenous fluid system, comprising:
providing an intravenous fluid system for use with a fluid bag, comprising
an inlet;
an outlet;
a passage through which a fluid may pass from the inlet to the outlet; and
an air removal device disposed between the inlet and the outlet, the air removal device configured to passively remove air from the fluid; the air removal device comprising an air chamber comprising a variable internal volume;
preventing the flow of fluid through the passage with a clamping device;
inserting the inlet into the fluid bag such that the passage is in fluid communication with the interior of the fluid bag;
releasing the clamp to allow fluid to enter the passage until the fluid reaches the outlet, passing through the air removal device;
preventing the flow of fluid through the passage with the clamping device;
increasing the internal volume of the air chamber; and
releasing the clamp to allow fluid to flow through the passage such that the air removal device removes air from the fluid.

16. The method of claim 15, wherein increasing the internal volume of the air chamber draws fluid from the passage into the air chamber.

17. A method of claim 15, further comprising:
inserting a portion of the intravenous fluid system into a pump, the pump configured to draw the fluid through the passage; and
activating the pump.

18. The method of claim 17, wherein the intravenous fluid system comprises a cassette disposed between the air removal device and the outlet, the cassette configured to interface with the pump.

* * * * *